United States Patent [19]

Rodak

[11] Patent Number: 5,190,203
[45] Date of Patent: Mar. 2, 1993

[54] CONTROLLED CLOSURE MECHANISM

[75] Inventor: Daniel Rodak, Milford, Conn.

[73] Assignee: United States Surgical Corporation, Norwalk, Conn.

[21] Appl. No.: 893,899

[22] Filed: Jun. 4, 1992

Related U.S. Application Data

[63] Continuation of Ser. No. 593,697, Oct. 5, 1990, abandoned.

[51] Int. Cl.$^5$ .............................................. A61B 17/72
[52] U.S. Cl. ...................................... 227/175; 227/19; 227/178
[58] Field of Search ................ 227/175, 176, 178, 182, 227/20, 29, 152, 153; 403/DIG. 9; 29/243.056; 269/6

[56] References Cited

U.S. PATENT DOCUMENTS

| | | | |
|---|---|---|---|
| 3,080,564 | 3/1963 | Strekopitov et al. | 227/153 |
| 3,252,643 | 5/1966 | Strekopitov et al. | 227/109 |
| 3,269,630 | 8/1966 | Fleischer | 227/107 |
| 3,275,211 | 9/1966 | Hirsch et al. | 227/124 |
| 3,494,533 | 2/1970 | Green et al. | 227/19 |
| 3,589,589 | 6/1971 | Akopov | 227/153 |
| 3,692,224 | 9/1972 | Astafiev et al. | 227/19 |
| 3,795,034 | 3/1974 | Strekopytov et al. | 29/212 D |
| 3,822,818 | 7/1974 | Strekopytov et al. | 227/124 |
| 3,935,981 | 2/1976 | Akopov et al. | 227/19 |
| 3,949,923 | 4/1976 | Akopov et al. | 227/19 |
| 4,047,654 | 9/1977 | Alvarado | 227/19 |
| 4,111,206 | 9/1978 | Vishnevsky et al. | 227/19 X |
| 4,272,002 | 6/1981 | Moshofsky | 227/19 |
| 4,305,539 | 12/1981 | Korolkov et al. | 227/8 |
| 4,354,628 | 10/1982 | Green | 227/152 X |
| 4,378,901 | 4/1983 | Akopov et al. | 227/19 |
| 4,383,634 | 5/1983 | Green | 227/135 X |
| 4,402,445 | 9/1983 | Green | 227/19 |
| 4,442,964 | 4/1984 | Becht | 227/19 X |
| 4,470,533 | 9/1984 | Schuler | 227/19 |
| 4,485,811 | 12/1984 | Chernousov et al. | 128/303.1 |
| 4,506,670 | 3/1985 | Crossley | 227/15 X |
| 4,506,671 | 3/1985 | Green | 227/19 X |
| 4,513,746 | 4/1985 | Aranyi et al. | 227/19 X |
| 4,527,724 | 7/1985 | Chow et al. | 227/19 X |
| 4,585,153 | 4/1986 | Failla et al. | 227/19 X |
| 4,589,582 | 5/1986 | Bilotti | 227/19 |
| 4,591,085 | 5/1986 | Di Giovanni | 227/8 |
| 4,605,004 | 8/1986 | Di Giovanni | 112/169 X |
| 4,606,344 | 8/1986 | Di Giovanni | 112/169 X |
| 4,606,345 | 8/1986 | Dorband et al. | 112/169 X |
| 4,607,636 | 8/1986 | Kula et al. | 128/334 R |
| 4,611,595 | 9/1986 | Klieman et al. | 227/19 X |
| 4,615,474 | 10/1986 | Strekopytov et al. | 227/19 X |
| 4,643,190 | 2/1987 | Heimberger | 128/321 |
| 4,665,916 | 5/1987 | Green | 227/19 X |
| 4,669,647 | 6/1987 | Storace | 227/19 |
| 4,684,051 | 8/1987 | Akopov et al. | 227/19 |
| 4,728,020 | 3/1988 | Green et al. | 227/19 |
| 4,741,336 | 5/1988 | Failla et al. | 227/19 X |
| 4,788,978 | 12/1988 | Strekopytov et al. | 128/334 R |
| 4,848,637 | 7/1989 | Pruitt | 227/19 |
| 4,915,100 | 4/1990 | Green | 227/176 |
| 4,930,503 | 6/1990 | Pruitt | 227/178 |
| 4,941,623 | 7/1990 | Pruitt | 227/19 |

FOREIGN PATENT DOCUMENTS

| | | |
|---|---|---|
| 0067743 | 12/1982 | European Pat. Off. . |
| 0240722 | 10/1987 | European Pat. Off. . |
| 0246870 | 11/1987 | European Pat. Off. . |
| 0220437 | 4/1961 | Fed. Rep. of Germany . |
| 2542188 | 9/1984 | France . |
| 549145 | 5/1977 | U.S.S.R. . |
| 2066723 | 7/1981 | United Kingdom . |

*Primary Examiner*—Douglas D. Watts
*Assistant Examiner*—Kenneth E. Peterson
*Attorney, Agent, or Firm*—Thomas R. Bremer; Peter G. Dilworth; Rocco S. Barrese

[57] ABSTRACT

A surgical stapling or fastening instrument for applying surgical staples or fasteners to tissue having a controlled closure mechanism to approximate the distance between the jaw members of the instrument. The controlled closure mechanism consists of a catch member having a resilient material secured thereto which engages a pivotable lance member which freezes the rotation of the catch member at an infinite number of desired locations along its path of rotation. Controlling the position of the catch member controls the distance between the jaw members of the stapling or fastening device.

28 Claims, 8 Drawing Sheets

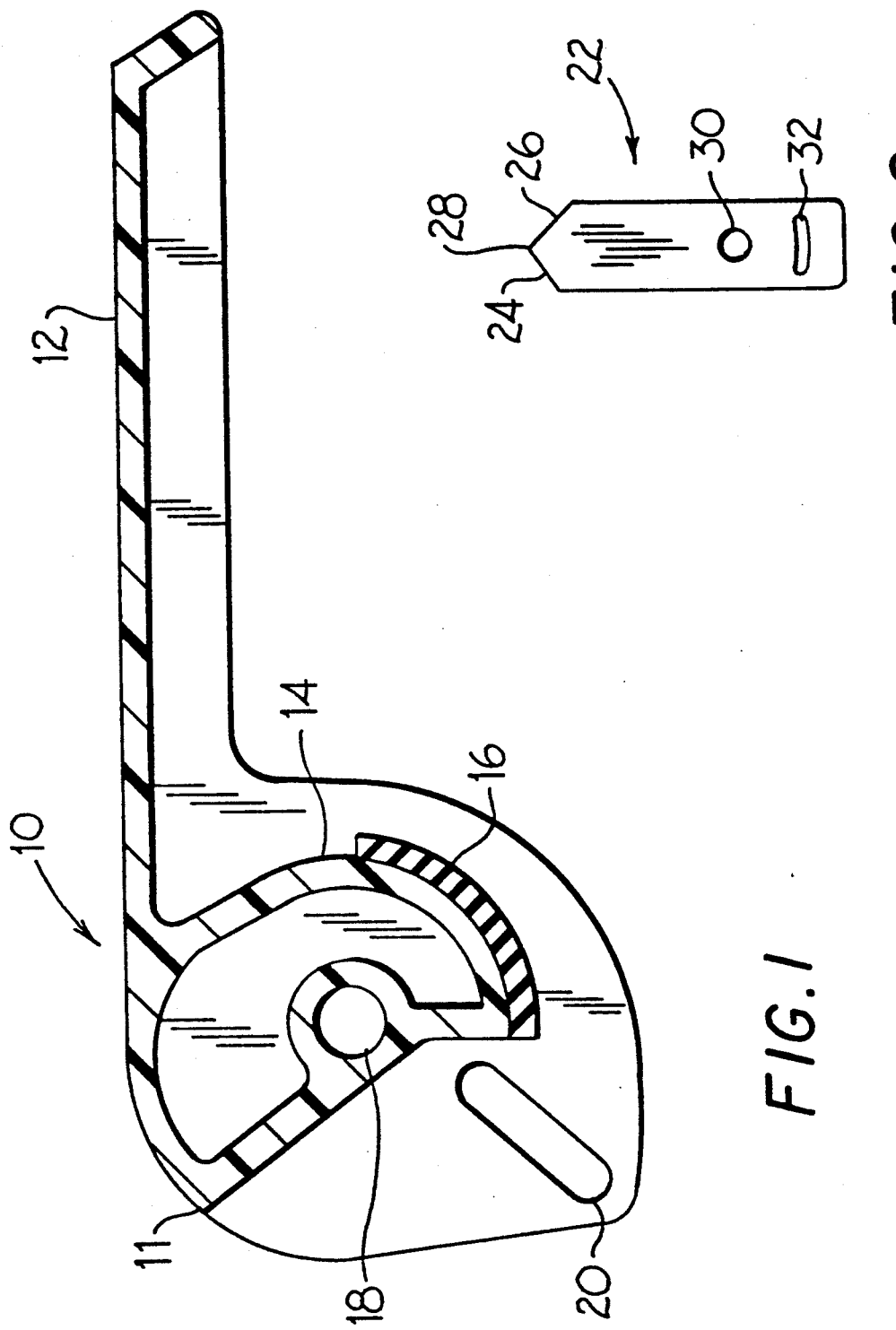

CONTROLLED CLOSURE MECHANISM

This is a continuation of copending application Ser. No. 07/593,697 filed on Oct. 5, 1990, now abandoned.

BACKGROUND OF THE INVENTION

1. Field of the Invention

The present invention relates to surgical instruments for applying surgical fasteners or staples to body tissue, and more particularly to controlled closure mechanisms for controlling the spacing between the jaw members between which the tissue passes during the fastening or stapling procedure.

2. Discussion of the Prior Art

Surgical stapling or fastening devices having means for controlling the spacing between the jaw members are well known in the art. These devices typically include indicating means to provide a reading of the spacing between the jaw members.

Various controlled closure mechanisms are provided in the prior art for use with surgical stapling and fastening devices. The most notable of these devices utilize a complex worm gear type arrangement or screw bearing member to open and close the spacing between the jaw members of the surgical stapling or fastening apparatus. These devices generally provide a rotatable knob or wing-like assembly at the trigger end of the device remote from the jaw mechanism which carries the staple or fastener cartridge. A screw like mechanism is used to open and close the spacing between the jaws. As the jaw members are fit around a tissue site to which the staples or fasteners are to be applied, the surgeon must grasp the device with one hand while rotating the knob or wing-like assembly with the other hand. As the jaw members close about the tissue to pinch the tissue therebetween, the surgeon then activates the trigger mechanism to drive the staples or fasteners into the tissue. Several known devices provide an indicator means near the rotatable knob which gives a visual indication of the spacing between the jaw members.

The prior art devices are subject to several disadvantages in both use and construction which render these devices difficult to operate and expensive to manufacture. Many of the devices are cumbersome in use in that the surgeon must operate the device with both hands, holding the body of the instrument in one hand, while rotating the knob or wing assembly with the other hand. This may lead to inaccurate stapling or fastening since the surgeon is unable to guide the tissue to be stapled or fastened with his free hand while closing the jaws about the tissue. Furthermore, the number of interacting components provides inaccuracies due to normal buildup of tolerances. In addition, the gear arrangement may become worn during extended use, thus rendering an imprecise grasping action at the jaws.

Furthermore, the prior art devices generally involve a complex construction in which a precisely machined or cast worm gear must be constructed and incorporated into the device. This of course increases the cost of manufacture, and requires a complex assembly procedure to properly locate the worm gear in the instrument to control the spacing between the jaws.

Typical devices having a rotatable knob at the end portion adjacent the handle mechanism of a surgical stapling or fastening device are disclosed in, among others, U.S. Pat. No. 4,930,503 to Pruitt, U.S. Pat. No. 4,788,978 to Strekopytov et al., and U.S. Pat. No. 4,606,344 to Di Giovanni. In each of these devices, an elongated rod member having screw threads machined thereon is provided. The rod member connects a rotatable knob positioned adjacent the handle members to a pusher mechanism which urges a movable jaw in a forward direction toward a stationary jaw to close the spacing between the jaw members. When a desired spacing is reached, the trigger mechanism may be activated to fire the staples or fasteners through the tissue into the anvil member mounted on the stationary jaw. To remove the stapling or fastening instrument after application of the staples or fasteners, the knob is rotated in an opposite direction which turns the screw threaded rod to move the movable jaw member away from the stationary jaw member so that the entire device may be removed from the tissue.

Surgical stapling or fastening instruments having a wing-like arrangement positioned adjacent the handle assembly of the device for moving a movable jaw toward a stationary jaw for affixing surgical staples or fasteners to tissue are disclosed in U.S. Pat. No. 4,442,964 to Becht and U.S. Pat. No. 3,795,034 to Sterkopytov et al. These devices are similar to those described above except for the provision of a rotatable wing member in place of the rotatable knob. These devices also provide a screw threaded rod member which, when rotated, urges a movable jaw towards a stationary jaw to close the spacing between the jaw members around tissue to be stapled or fastened. After the application of surgical staples or fasteners, the wing assembly is rotated in an opposite direction to draw the movable jaw away from the stationary jaw so that the instrument may be removed from the tissue.

The novel surgical stapling or surgical fastening device of the present invention obviates the disadvantages encountered in the prior art and provides an efficient controlled closure mechanism for controlling the spacing between the jaw members of the surgical stapling or fastening apparatus. The device of the present invention allows a surgeon to operate a surgical stapler or fastener with one hand while freeing the other hand to assist in the surgical procedure. Furthermore, the present invention is of lightweight construction and provides ease of handling by a thumb controlled closure mechanism which permits the surgeon to set the spacing between the jaw members and fire the device while using only one hand.

SUMMARY OF THE INVENTION

The present invention provides a novel closure mechanism for a surgical stapling or fastening device which controls the closing of the jaw mechanism to approximate the distance between the jaw members prior to activation of the trigger mechanism to fire the staples or fasteners. A thumb activated closure mechanism is provided which allows a surgeon to adjust the spacing between the jaw members and to fire the device using a single hand, which in turn allows the surgeon to use the other hand to assist the surgical procedure. The controlled closure mechanism of the present invention eliminates many moving parts associated with prior devices, and results in a lightweight, easy to use accurate surgical stapling or fastening device which is inexpensive to manufacture and relatively simple to assemble.

The controlled closure mechanism of the present invention may be used with any surgical instrument having jaw members which include a stationary jaw and a movable jaw, or two movable jaws, in which the spacing between the jaw members is adjustable to accommodate various thicknesses of tissue to be secured. The elimination of numerous complex moving parts which are common in the prior art devices allows the surgeon to approximate the distance between the jaw members in a fast and efficient manner to position the jaws in the proper alignment for the application of surgical staples or fasteners.

The controlled closure mechanism of the present invention comprises pivotal means for engaging the means for displacing (approximating) the jaw members. The pivotal means preferably comprises a catch member having a generally arcuate, preferably circular, body portion and a handle member which extends away from the body portion. A layer of resilient material is secured to the body portion and generally comprises an arcuate path extending in a concentric manner about the pivot point of the body portion. The resilient material is engaged by a lance member which penetrates the resilient material to lock the catch member in place.

The catch member and lance member are incorporated into the handle portion of a surgical stapling or fastening apparatus, and the catch member is rotatable about a pivot point provided in the stapling or fastening apparatus. The lance member is pivotably positioned on a boss member in the handle of the device and has a piercing tip which is adapted to engage the resilient material.

When the catch member is in an open position, the lance member is pivoted away from the resilient material and is maintained in this position by a biasing spring. As the catch member is rotated (pivoted) to its closed position, it slides over the lance. Thus the lance allows for free rotation of the catch member. Rotation of the catch member moves a camming arm which drives a cartridge driver member towards the jaw mechanism. The cartridge driver approximates the jaw(s) to pinch tissue therebetween. When the rotation of the catch member is stopped prior to reaching its closed position, (i.e. an intermediate position), the jaw(s) freezes in position while the lance penetrates the resilient member to lock (retain) the catch member in place. When the closing motion of the catch member is restarted, the catch member forces the lance member to pivot forward to its biased position to thereby provide for continued free motion of the catch member. This mechanism thus allows the surgeon to lock the jaw(s) in any desired position with any desired compression force during the closing process independent of the combined thickness of the body tissue.

To open the jaw mechanism after it is stopped at an intermediate position, a reverse motion of the catch member causes the lance member to rotate over center to a rearward position, thus overcoming the spring force of the resilient material and allows free motion of the catch member. When the catch member is moved to its fully opened position, the lance member no longer engages the resilient material. The lance pivots due to its biasing spring back to its original position upon rotation of the catch member towards its closed position.

BRIEF DESCRIPTION OF THE DRAWINGS

The foregoing objects and other features of the present invention will become more readily apparent and may be understood by referring to the following detailed description of an illustrative embodiment of the surgical stapling or fastening instrument and its novel controlled closure mechanism, taken in conjunction with the accompanying drawings, in which:

FIG. 1 illustrates a side plan view, partially in cross-section, of the catch mechanism of the present invention;

FIG. 2 illustrates a side plan view of the lance member of the present invention;

DETAILED DESCRIPTION OF THE PREFERRED EMBODIMENTS

Figure 8:
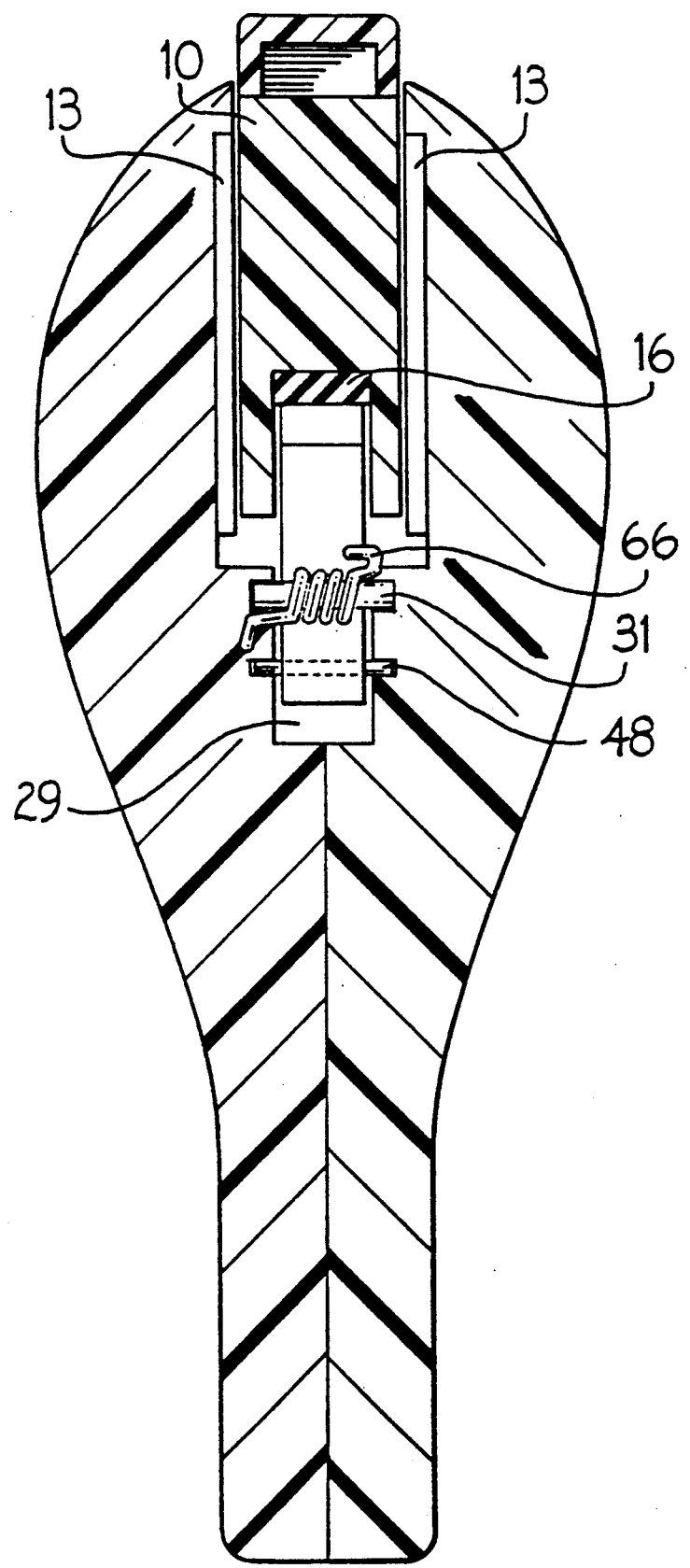
FIG. 8 illustrates a rear sectional view of the handle of a surgical stapling or fastening instrument showing the controlled closure mechanism of the present invention is an intermediate position.

Referring now in specific detail to the drawings, in which like reference numerals identify similar or identical elements throughout the several views, FIG. 1 shows the catch member 10 of the controlled closure mechanism of the present invention. Catch member 10 has a generally circular shaped body portion 11 having an elongated handle member or lever 12 extending outwardly therefrom. Lever 12 extends outwardly from the instrument housing for easy access by the user (see FIG. 3). The catch member 10 is seated within frames 13 of the instrument housing as shown in FIG. 8. The catch mechanism 10 extends about pivot point 18 and also includes an arcuately shaped surface 14, upon which a resilient material 16 is secured preferably by cyanoacrylate or other suitable adhesive. Thus, the resilient material 16 comprises an arcuate path extending in a concentric manner about the pivot point. Resilient material 16 is preferably a rubber type material, such as Silastic ® of Dow Corning, but may include any soft rubber-like material. The length of the resilient material 16 preferably ranges from 1.25 to 0.875 inches depending on the length of the surface 14 and the arc over which surface 14 travels. The thickness of the resilient material 16 preferably ranges between 0.125 and 0.050 inches. Clearly, resilient material of other lengths and thickness can be provided to achieve the functions described herein. Catch mechanism 10 is further provided with a cam slot 20 whose function will be described hereinbelow.

Figure 3:
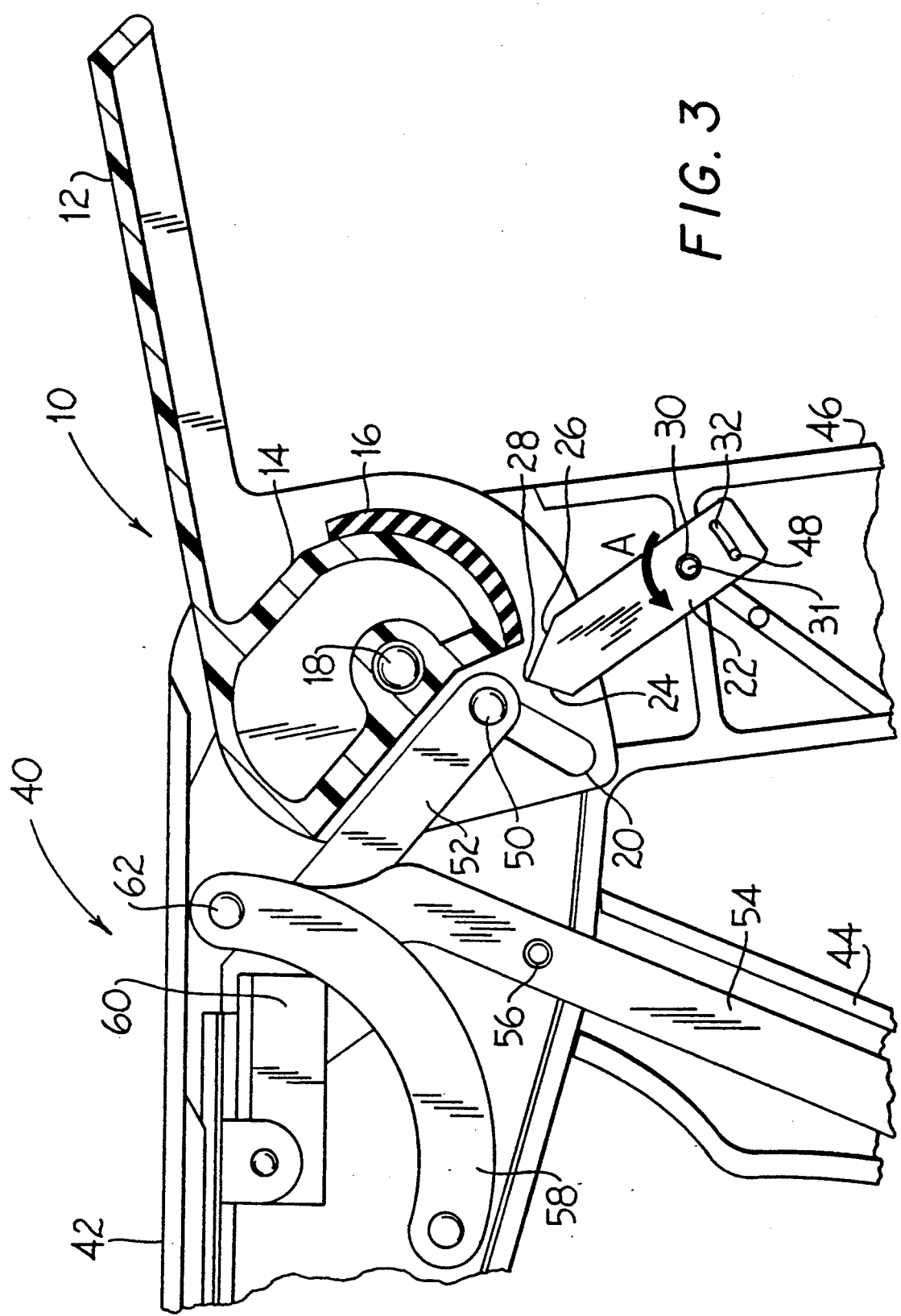
FIG. 3 illustrates a side cutaway view of the handle of a surgical stapling or fastening instrument employing the controlled closure mechanism of the present invention in which the catch mechanism is in the open position and the trigger mechanism is in the unfired position.
Figure 4:
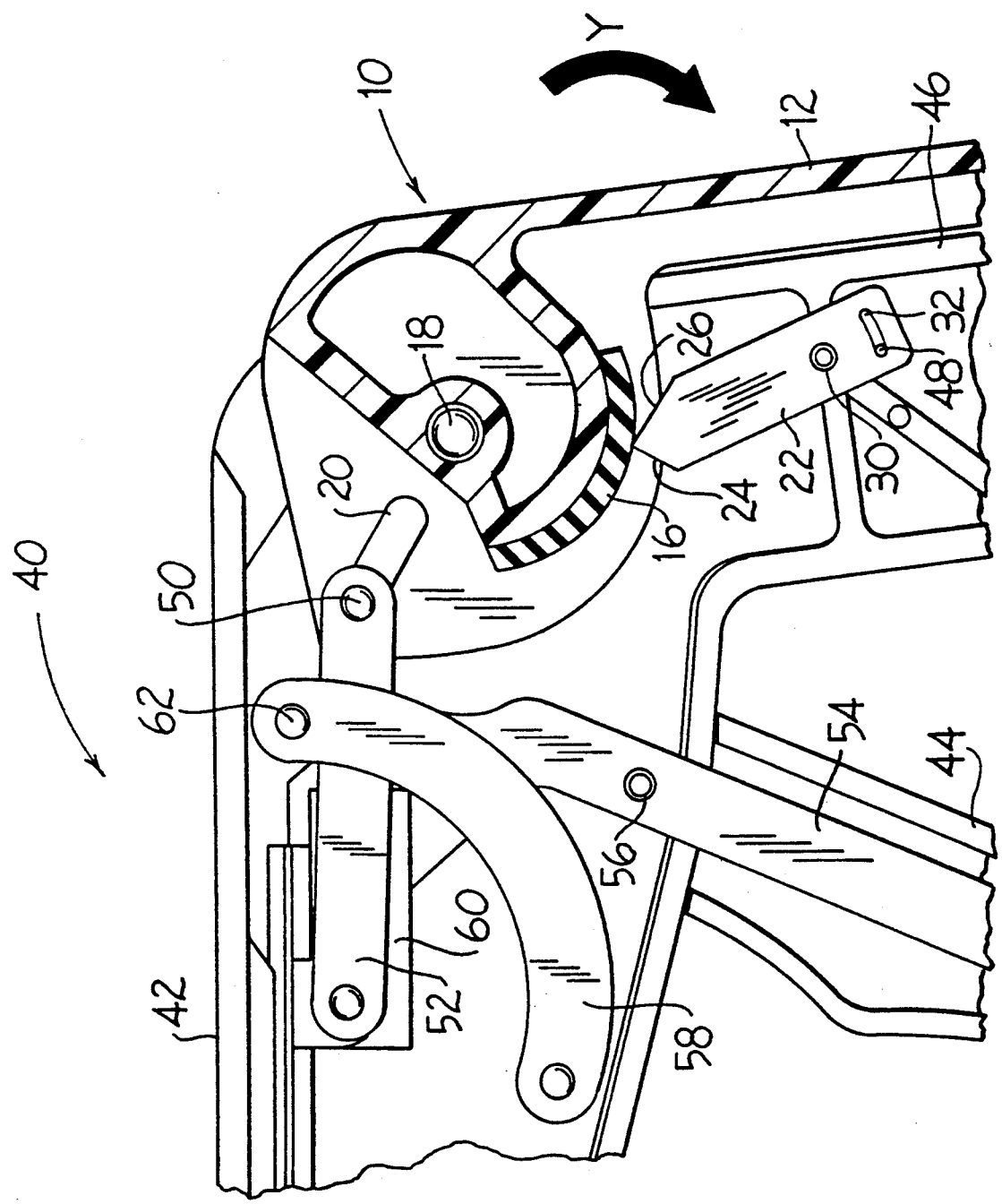
FIG. 4 illustrates a side cutaway view of the handle of a surgical stapling or fastening instrument in which the controlled closure mechanism of the present invention is in the closed position and the trigger mechanism is in the unfired position.

FIG. 2 shows the lance member 22 of the controlled closure mechanism of the present invention, which is positioned and configured to allow unimpeded continuous rotation of arcuate surface 14 from an open position (e.g., FIG. 3) to a closed position (e.g., FIG. 4). Lance member 22 is secured within a cavity 29 formed in the housing of the instrument as shown in FIG. 8 and is adapted to engage resilient material 16 to retain the catch member 10 in a locked position when the lever 12 is stopped during the closure motion (i.e. at any intermediate position) which will be described in detail below.

Lance member 22 is provided with a pair of angled face surfaces 24 and 26. Face 26 has an angle which allows for the free rotation of the catch member 10 during the closing motion as it is tangent to the outer surface of material 16. Face 24 has an angle which allows for free rotation of the catch member 10 during the opening rotation of catch mechanism 10 as it is also tangent to the outer surface of material 16. Faces 24 and 26 meet at a piercing point 28, which engages and penetrates resilient material 16 when the motion of lever 12 is stopped to thereby lock the catch member 10 in position. A pivot aperture is provided as at 30 to mount the lance member 22 on a suitable boss in the handle of the surgical stapling or fastening instrument by a pin 31, as seen in FIGS. 3 through 8. A guide slot 32 is also provided to limit the pivoting rotational movement of lance member 22.

Figure 6:
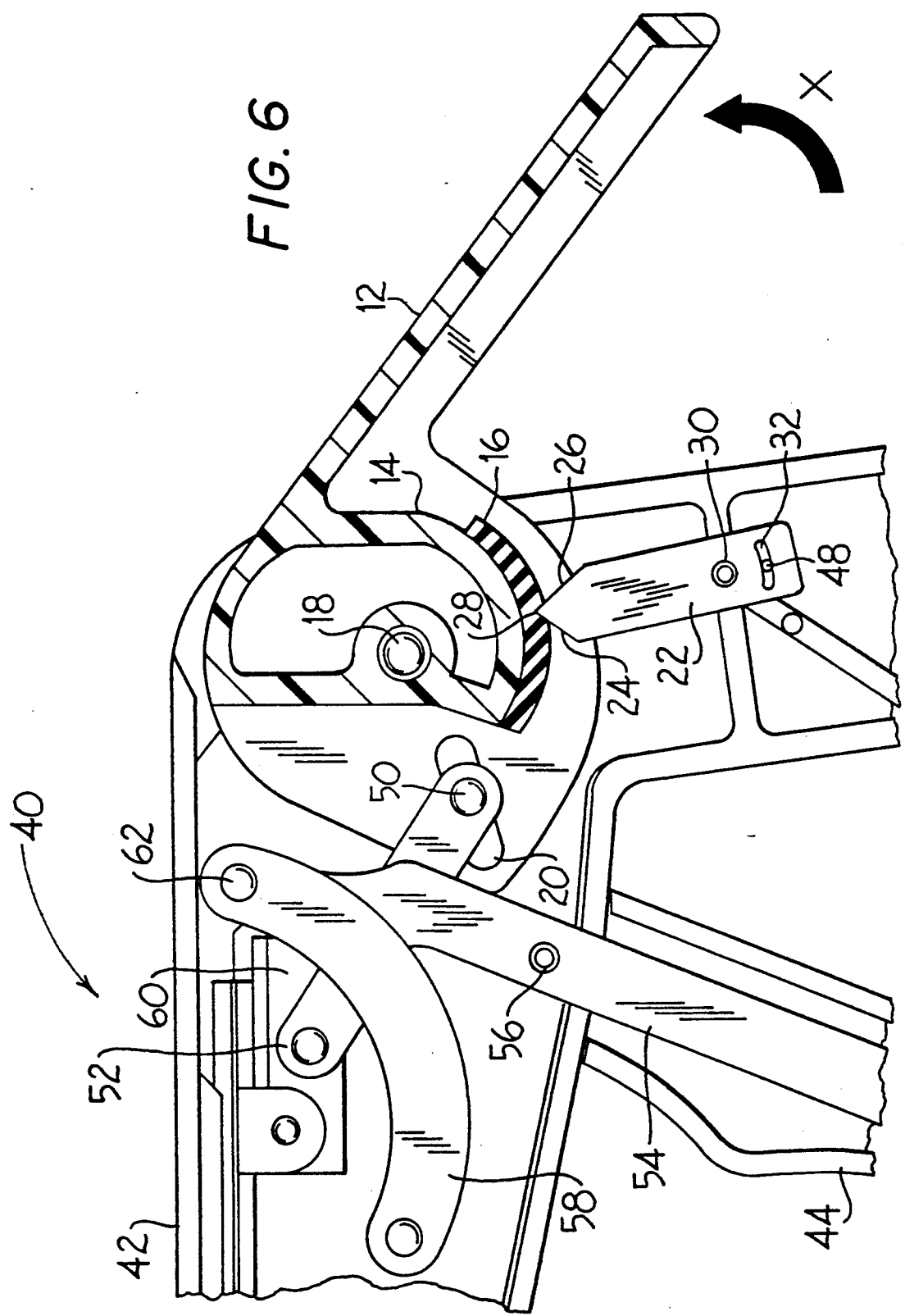
FIG. 6 illustrates a side cutaway view of a surgical stapling or fastening instrument in which the controlled closure mechanism of the present invention is in an intermediate position and the trigger mechanism is in the unfired position.

The catch member 10 is pivotable about pin 31 from an open position as shown in FIG. 3 to a closed position as show in FIG. 4 by movement of lever 12 in a clockwise (downward) direction (see arrow y of FIG. 4). The rotation of the catch member 10 can advantageously be interrupted at an infinite number of points between the open and closed position. FIG. 6 illustrates one of these intermediate positions where the catch member 10 is effectively frozen in position at a middle point along its arcuate path.

Turning now to FIG. 3, a surgical stapling or fastening instrument 40 is shown in a cutaway view of the handle end of the device. FIG. 3 illustrates the catch member 10 in the open position, in which the jaw mechanism (not shown) is also in its openmost position. The device of FIG. 3 is shown with the trigger for firing the staples or fasteners in the unfired position.

When the catch member 10 is in the position shown in FIG. 3, handle 12 is in its upmost position away from instrument handle 46. In this position, resilient material 16 is positioned away from lance member 22, which is spring biased in a counterclockwise direction (arrow A of FIG. 3) by a torsion spring 66 (FIG. 8). That is, piercing point 28 of lance member 22 is maintained in the unengaged position (i.e. not in contact with resilient material 16) when catch member 10 is at the orientation shown in FIG. 3. A guide post 48 engages guide slot 32 to restrict rotation of lance member 22 about pivot point 30. Clearly, other means for limiting rotation of lace member 22 could alternately be provided.

Although FIG. 3 shows the resilient material 16 spaced from piercing point 28 when in the open position, in an alternate embodiment, a longer piece of silastic material could be provided so that it is contiguous with lance member 22 when the catch member 10 is in the open position.

FIG. 3 further shows trigger member 44 in the unfired position. Trigger arm 54 enters body 42 and is pivoted about trigger pivot 56 in its forwardmost position, such that trigger drive 58 is held in a rearward position.

Cam slot 20 of catch member 10 is positioned as shown in FIG. 3 in which bearing post 50 is urged to one end of cam slot 20 to draw cam arm 52 in a rearward (proximal) direction. When cam arm 52 is in this position, a cartridge driving mechanism 60 is also in a rearward (proximal) position so that the stapling or fastening mechanism at the jaw members may not be fired.

FIG. 4 illustrates the catch mechanism 10 in the closed position with the trigger mechanism in the unfired position. As best seen in FIG. 4, lever 12 has been moved clockwise in the direction of arrow y to its lowermost position to abut the handle member 46 of the instrument housing. The lance member 22 remains spring biased counterclockwise. The angled surface 26 remains tangent to the resilient material 16 during the entire continuous clockwise rotation of catch member 10 so that lance member 22 does not impede the rotational movement of catch member 10. The rearward directed force of link 52 maintains lever 12 in its position.

As catch member 10 is rotated to the position shown in FIG. 4, bearing post 50 slides in cam slot 20 to move cam arm 52 to the position shown in FIG. 4. Movement of cam arm 52 slides cartridge driver 60 distally to close the distance between the jaw members at the stapling or fastening end of the instrument to grip body tissue therebetween. In the position shown in FIG. 4, stapling or fastening instrument 40 is ready to be fired.

Figure 5:
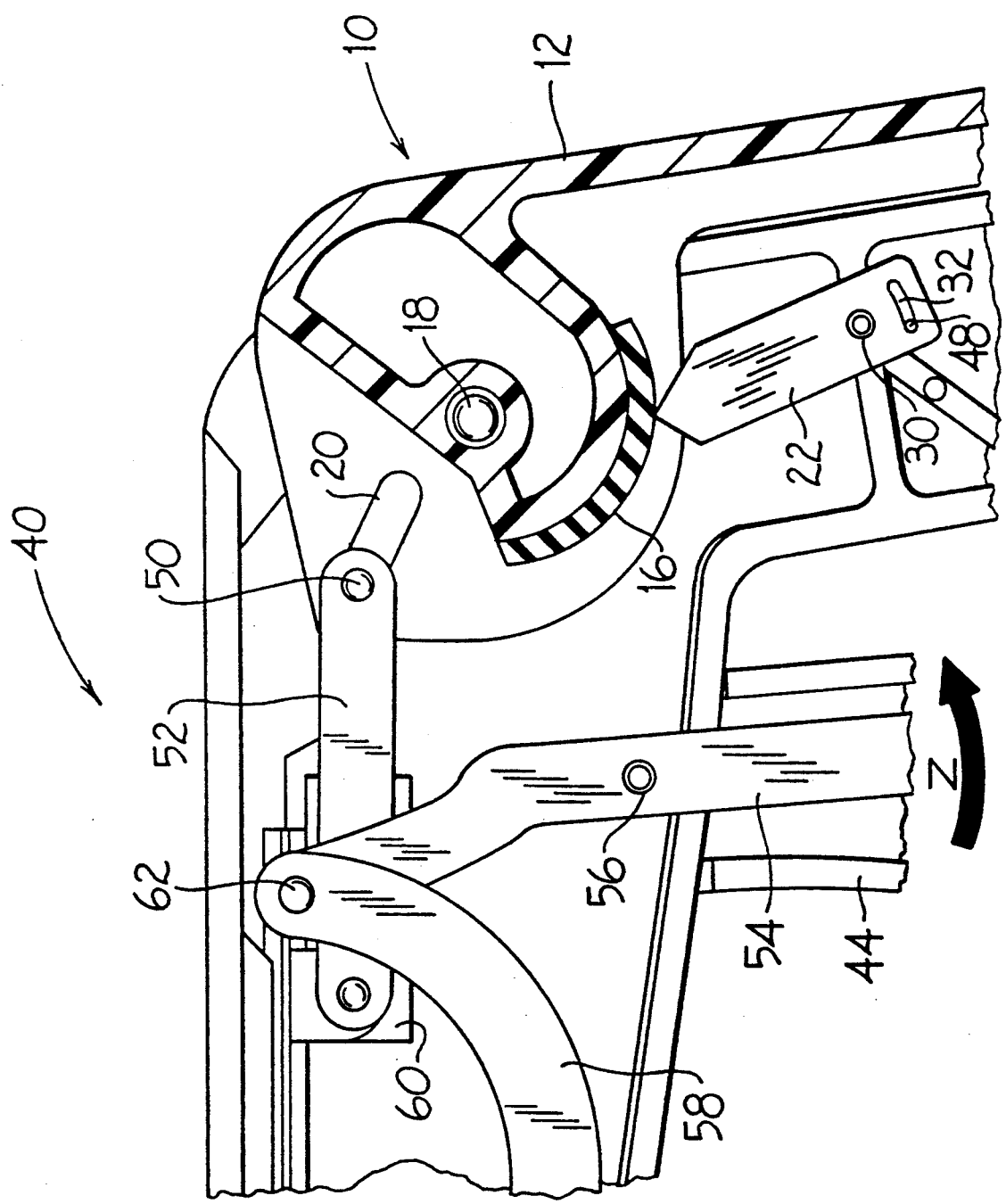
FIG. 5 illustrates a side cutaway view of the handle of a surgical stapling or fastening instrument in which the controlled closure mechanism of the present invention is in the closed position and the trigger mechanism is in the fired position.

Turning now to FIG. 5, instrument 40 is shown with the catch member 10 corresponding to the jaws in the closed position as in FIG. 4 and the trigger member 44 in the fired position. Catch member 10 and lance member 2i are in the same position as shown in FIG. 4, with cam arm 52 urging cartridge driver 60 into the closed position to bring the jaws into position. As the trigger member 44 is moved proximally toward handle member 46 (see arrow z), trigger arm 54 pivots about trigger pivot point 56 to drive trigger driver 58 forward to actuate a driver to fire the staple(s) or fastener cartridge(s). Trigger driver 58 is driven forward by trigger arm 54 through connection point 62 as shown.

After firing the cartridge, the trigger member 44 returns to its forward position shown in FIG. 4. The handle member 12 is then rotated in a counterclockwise (upward) direction to the open position shown in FIG. 3 (see arrow x of FIG. 6) and catch member 10 correspondingly rotates to slide cam arm 52 proximally to thereby move the cartridge driver 60 back to its rearward position. Such counterclockwise rotation of catch member 10 causes lance member 22 to pivot rearwardly through the positions shown in FIGS. 6 and 7 until it reaches its rearmost position and lever 12 reaches its upwardmost position. At this position, the resilient material 16 clears lance member 22, thereby resulting in lance member 22 springing forward under the biasing force of its spring 66 to the position shown in FIG. 3.

In an alternate embodiment wherein the resilient material 16 is of a length so that there is no clearance between the lance member 22 and the resilient material 16 when catch member 10 is in its open position, lance member 22 will remain in its rearwardmost position until lever 12 is rotated clockwise to provide a sufficient force to urge lance member 22 to its forward position. Thus, in this embodiment, lance member 22 does not automatically spring forward when lever 12 is rotated to its upwardmost position.

As is clearly seen, in either embodiment lance member 22 does not impede movement of catch member 10 when lever 12 is moved uninterruptedly from its open position (FIG. 3) to its closed position (FIG. 4) and back to its open position (FIG. 4).

Following application of surgical staples or fasteners, trigger member 44 is returned from the position in FIG. 4 to the position shown in FIG. 3, and the device is ready to open and reload for use in applying additional staples or fasteners. When catch member 10 is rotated to the position shown in FIG. 3, cartridge driver 60 is drawn rearwardly to open the jaw members of the distal end of the stapling or fastening device 40. This allows the device to be removed from the area just stapled or fastened so that the device may be moved to another location.

Figure 7:
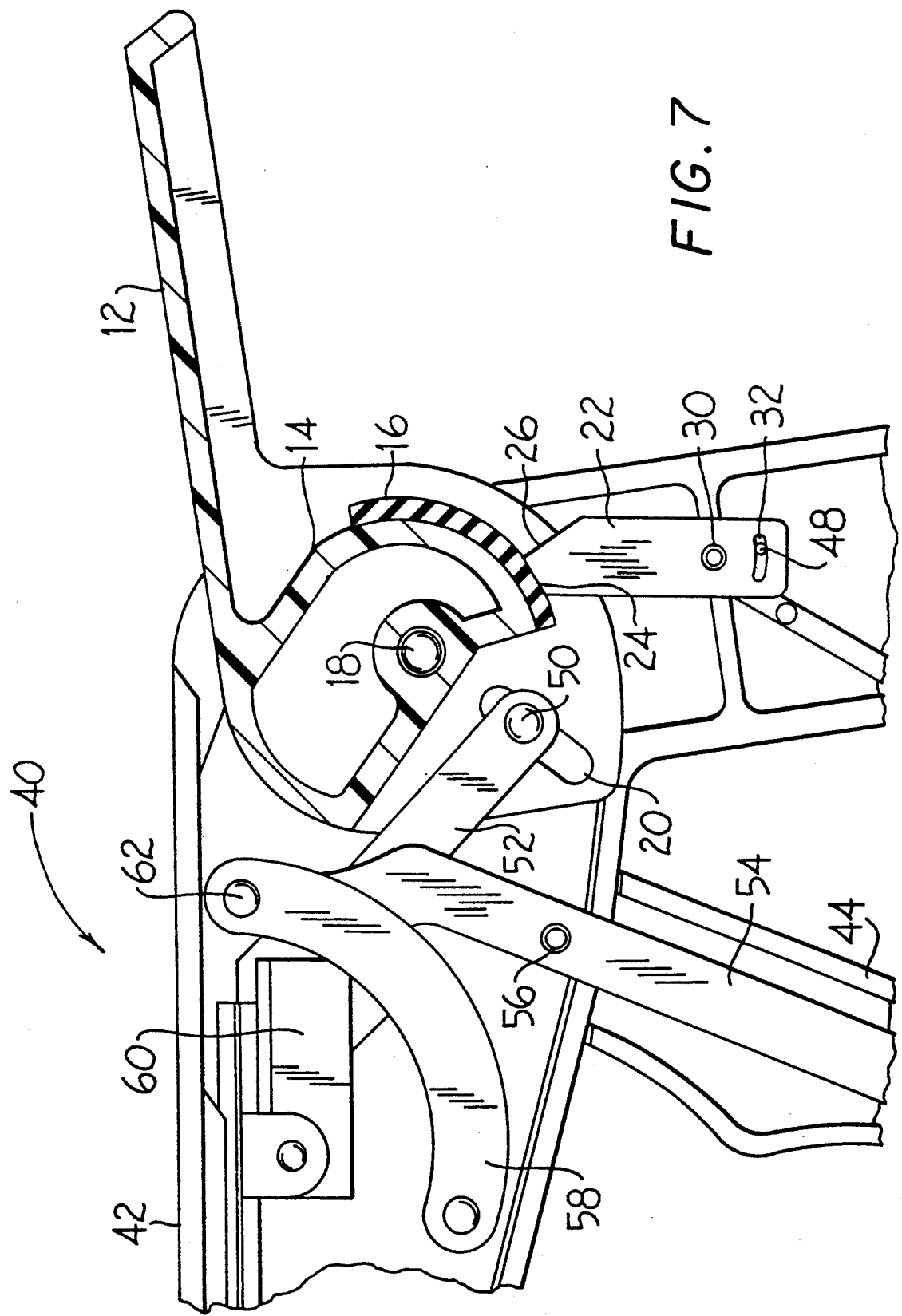
FIG. 7 illustrates a side cutaway view of a surgical stapling or fastening instrument in which the catch mechanism of the present invention is returning towards its open position from the intermediate position of FIG. 6.

As mentioned above, the closure mechanism of the present invention advantageously allows the catch member 10 to be frozen at any point in its arcuate path. With reference to FIGS. 6 and 7, when catch member 10 is stopped during its clockwise motion at an intermediate position, the force of link 52 urges the catch member 10 against the piercing point 28 of lance member 22, thereby overcoming the bias of spring 66 and causing lance member 22 to pivot rearwardly (clockwise) on pivot pin 31 to become embedded in the resilient material 16. Thus, the piercing point 28 prevents further rotation of catch member 10 which in turn stops movement of link 52 to effectively freeze movement of cartridge driver 60.

If the user desires to continue closing the lever 12 after "freezing" it, sufficient downward (clockwise) pressure on lever 12 will overcome the force of the resilient material 16 against piercing point 28, allowing lance member 22 to pivot forwardly to its biased position and the resilient material 16 to freely pass over angled surface 26 of lance member 22 as the catch member 10 is moved to the closed position shown in FIG. 4.

If the user desires to reopen the closure mechanism rather than close it after "freezing" it, an upward (counterclockwise) force on lever 12 will overcome the biasing force of spring 66 and resilient material 16 to urge lance member 22 rearwardly, thereby disengaging resilient material 16 from piercing point 28. Resilient material 16 will slide along angled surface 24 of lance member 22 as the catch member 10 is rotated towards its open position as shown in FIG. 7. Lance member 22 is thus forced to its rearmost position with guide post 48 in the rightmost position of guide slot 32 to limit further rearward movement. The force exerted on the catch member 10 by link 52 helps prevent the lance member 22 from returning to its normal forwardly biased position. The operator can thereafter rotate catch mechanism 10 towards its closed position by applying a downward force on lever 12 which will initially engage lance member 22, causing it to rotate over center and then to pivot in the direction of arrow "A" to its biased position as shown in FIG. 3.

Figure 9:
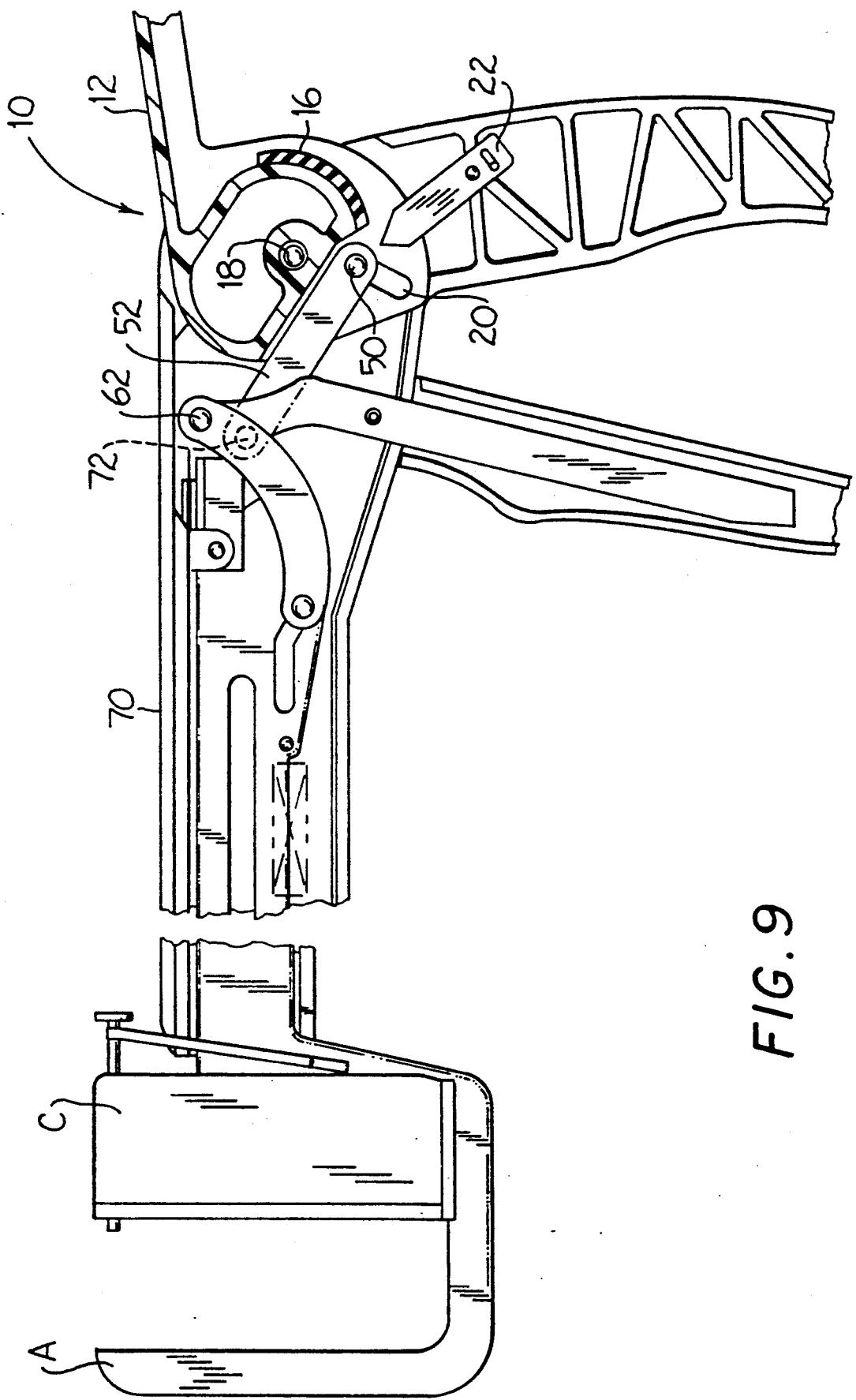
FIG. 9 illustrates a side view of one type of surgical stapling instrument employing the catch mechanism of the present invention.

As is clear from the description above, the closure mechanism of the present invention can be utilized with many types of surgical staple or surgical fastener instruments. In the embodiment of FIG. 9, which is shown by way of example, the closure mechanism is utilized in a surgical stapling instrument having a cartridge C longitudinally movable with respect to an anvil A. In this embodiment, lever 12 is shown in the open position and lance member 22 is shown in its forward biased position. When lever 12 is rotated clockwise to rotate catch member 10 in the same direction, link 52 slides to a longitudinal position shown in dotted line. This causes a longitudinally extending cartridge holder 70 to move via linkage pin 72 from a proximal position to a distal position (shown in dotted line). Distal movement of the cartridge holder 70 causes connected cartridge C to slide distally towards anvil A to secure the tissue therebetween and allow for subsequent firing of the staples in a manner known in the art and therefore not described herein.

In the instrument shown in FIG. 9, the lever 12 can be stopped ("frozen") in any intermediate position between the open position and the closed position to thereby control movement of cartridge C. Freezing of the lever 12 causes the lance member 22 to effectively hold the catch member 10 in the frozen position. This enables the operator to stop approximation of cartridge C and to adjust the spacing. The operator can then resume closing of the cartridge C by further clockwise rotational movement of lever 12 in the manner described above. Should the operator choose to return the jaws to a more opened position, the handle member 12 can be rotated upwardly (conterclockwise) to overcome the force of the resilient material as is also described above.

The closure mechanism of the present invention can also be used in other instruments to close the distance between a movable jaw member and a stationary jaw member at the stapling or fastening end of the instrument or between two movable jaw members. That is, the jaw mechanism may be of the type, wherein one jaw moves toward and away from the other; however, the present invention is also applicable for use with devices of alternative types, i.e., where both jaws move toward and away from each other. The surgical instrument may be of the type which applies metal staples or two-part fasteners of the bioabsorbable type.

The surgical stapling or fastening instrument employing the controlled closure mechanism of the present invention is a device which may be operated with one hand to effect the closure motion of the jaw members of the instrument followed by activation of the trigger mechanism to fire the staples or fasteners into the tissue. The complex arrangement of the prior are devices is eliminated, resulting in a lightweight and easy to handle instrument which is inexpensive to manufacture and easy to assemble.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for surgically applying closure means to body tissue, which comprises:
   a) first and second means for gripping the body tissue therebetween and for applying the tissue closure means, b) a longitudinally extending member cooperating with at least one of said first and second gripping means:

c) actuation means for driving said tissue closure means, d) means for displacing said longitudinally extending member to advance at least one of said first and second gripping means toward the other to grip the body tissue therebetween in preparation for applying the tissue closure means, said displacing means being independent of said actuation means; and e) means for engaging and disengaging said displacing means so as to retain said first and second gripping means in selective spaced relation to provide predetermined gripping force independent of thickness of the body tissue therebetween.

2. The apparatus according to claim 1, wherein said displacing means is a catch member having a generally arcuate surface portion.

3. The apparatus according to claim 2, wherein said generally arcuate surface portion is circular.

4. The apparatus according to claim 2, wherein said circular surface portion is comprised of an elastomeric material.

5. The apparatus according to claim 4, wherein said catch member is mounted for pivotal rotation such that said elastomeric surface portion rotates about a pivot point of said catch member.

6. The apparatus according to claim 5, wherein said means to engage said displacing means comprises a pivotable lance member having a sharp end portion adapted to engage said elastomeric surface portion.

7. The apparatus according to claim 6, wherein said lance member is mounted for pivotal rotation adjacent said catch member.

8. The apparatus according to claim 7, wherein pivotal rotation of said catch member causes at least one gripping means to be displaced toward the other gripping means to allow activation of a fastener firing system.

9. The apparatus according to claim 8 wherein said lance member is rotatably resilient biased toward a distal end of the apparatus.

10. An apparatus as recited in claim 9, wherein said lance member comprises a slot formed therein to receive a post to limit pivotal movement of said lance member.

11. An apparatus as recited in claim 6, wherein said lance member has first and second angled surfaces intersecting at a tip of said sharp end, said angled surfaces dimensioned to allow continuous rotation of said catch member without interference from said lance member.

12. The apparatus according to claim 11, wherein said catch member is pivotable between an open position and a closed position, and said lance member engages said elastomeric material of said catch member when pivotable movement of said catch member is stopped at a position intermediate of said open and closed positions, said lance member thereby freezing said catch member in said intermediate position.

13. An apparatus as recited in claim 12, wherein rotatable movement of said catch member from said closed position or said intermediate position to said open position causes said lance member to pivot towards a proximal end of the apparatus.

14. An apparatus as recited in claim 13, wherein pivotal movement of said catch member from said intermediate position to said closed position causes said lance member to pivot toward a distal end of the apparatus to return to its biased position.

15. Apparatus for surgically applying closure means to body tissue wherein two jaw members are positioned in adjacent relation, at least one jaw member being movable toward and away from the other for gripping the body tissue, applying the tissue closure means and releasing the body tissue, and a longitudinally extending member cooperating with said movable jaw member, said apparatus comprising pivotally mounted means for advancing said longitudinally extending member for approximating spacing between said jaw members and pivotable means associated with said advancing means for retaining said jaw members selectively in any of a plurality of fixed relative spaced positions to grip the body tissue, said retaining means being pivotable on an axis fixedly spaced relative to the axis of the pivotable advancing means.

16. An apparatus as recited in claim 15, wherein said pivotal approximating means comprises a catch member pivotable clockwise from an open position to a closed position.

17. An apparatus as recited in claim 16, wherein said catch member comprises an elongated lever extending outwardly therefrom and protruding through a housing of the apparatus.

18. Apparatus as recited in claim 15, further wherein said retaining means engages a surface portion of said pivotal approximating means to thereby retain the position of said approximating means.

19. Apparatus for surgically applying closure means to body tissue wherein two jaw members are positioned in adjacent relation and at least one jaw member is movable toward and away from the other for gripping the body tissue and applying closure means to the body tissue, said apparatus comprising pivotal means for approximating said jaw members sufficient to grip the body tissue therebetween and for moving at least one of said jaw members away from the other to release the body tissue, said approximating means including a surface portion comprised of resilient material, means mounted adjacent said resilient material and engagable therewith in a manner to retain said approximating means in any of a selective plurality of positions of said jaw members to apply selective force to said body tissue independent of thickness of the body tissue.

20. An apparatus as recited in claim 19, wherein said retaining means comprises a member having an end portion adapted to engage said resilient material.

21. An apparatus as recited in claim 20, wherein said member is a lance member having a pointed end portion.

22. An apparatus as recited in claim 19, wherein said resilient material is an elastomeric material.

23. An apparatus as recited in claim 19, wherein said surface portion of said approximating means is arcuately shaped.

24. Apparatus for surgically applying closure means to body tissue wherein a pair of jaws are adapted to grip the body tissue and apply the closure means, the jaws being movable between a first position in close adjacent relation and a second relatively spaced position whereby the tissue may be released, the apparatus comprising:

a) a longitudinally extending member cooperating with at least one of said jaws;

b) pivotable approximating means connected to said longitudinally extending member and pivotable between two end positions corresponding to said first and second positions of said jaws;

c) means positioned adjacent at least a portion of said pivotable approximating means and adapted to engage and disengage said approximating means to retain the position of said approximating means corresponding to any of a plurality of spaced positions of said jaws with body tissue positioned therebetween.

25. Apparatus for applying closure means to body tissue which comprises:

a) body means;

b) at least two jaw members supported by said body means for gripping body tissue and for applying closure means;

c) pivotally mounted means associated with said jaw members for approximating said jaw members to grip the body tissue and for moving at least one of said jaw members away from the other to release the body tissue, said approximating means having an arcuate resilient compressible surface portion; and d) means pivotally mounted adjacent said arcuate resilient surface portion and engagable therewith in a manner to selectively retain said aproximating means in any of a plurality of pivotal positions corresponding to spaced positions of said jaw members to selectively apply force to body tissue therebetween independent of thickness of the body tissue.

26. An apparatus for surgically applying fastener means to body tissue, which comprises:

a) first and second means for gripping the body tissue therebetween and for applying the fastener means;

b) a longitudinally extending member cooperating with at least one of said first and second gripping means;

c) actuation means for driving said fastener means;

d) means for advancing said longitudinally extending member for approximating at least one of said first and second gripping means toward the other to grip the body tissue therebetween in preparation for applying the fastener means, said advancing means being independent of said actuation means; and e) means for engaging and disengaging said advancing means so as to retain said first and second gripping means in selective spaced relation to grip to body tissue.

27. An apparatus according to claim 26, wherein said engaging means comprises a catch member for engaging and gripping said approximating means.

28. An apparatus according to claim 27, wherein said catch member engages resilient material positioned on said approximating means.

* * * * *